United States Patent [19]
Whitlock et al.

[11] Patent Number: 5,147,365
[45] Date of Patent: Sep. 15, 1992

[54] PATELLAR OSTEOTOMY GUIDE

[75] Inventors: Steven I. Whitlock, Austin; Steven G. Brown, Pflugerville, both of Tex.

[73] Assignee: Intermedics Orthopedics, Inc., Austin, Tex.

[21] Appl. No.: 746,964

[22] Filed: Aug. 19, 1991

[51] Int. Cl.$^5$ ............................................. A61B 17/14
[52] U.S. Cl. ..................................................... 606/88
[58] Field of Search .................................. 606/86–91, 606/96, 79–85

[56] References Cited

U.S. PATENT DOCUMENTS

| | | | |
|---|---|---|---|
| 4,633,862 | 1/1987 | Petersen | 606/88 |
| 5,021,055 | 6/1991 | Burkinshaw | 606/87 |

Primary Examiner—Robert A. Hafer
Assistant Examiner—David J. Kenealy
Attorney, Agent, or Firm—John R. Merkling

[57] ABSTRACT

A patella osteotomy guide comprising a plier-like appliance with curved jaws for grasping a patient's patella. A row of teeth faces inwardly from the jaws. The teeth are generally of pyramid shape, but a vertex of each tooth lies in a plane containing a bottom side of the respective jaw. Each of the jaws has an integral saw capture slot and the tips of the jaws are extended. A rotating, calibrated stylus measures the position of the patella with respect to the integral saw capture slots. The rotating stylus also functions as a pivot or fulcrum about which the jaws and handles of the osteotomy guide rotate. Handles for the osteotomy guide are offset from the plane of the jaws. The rotating stylus can be displaced up and down and then locked into a selected position using a draw bar and captured balls. A bowed retaining ring imparts a certain amount of pre-load to the stylus and draw bar assembly to hold the assembly in a selected position.

16 Claims, 2 Drawing Sheets

PATELLAR OSTEOTOMY GUIDE

BACKGROUND OF THE INVENTION

Our invention relates to orthopedic surgical guides and jigs. Specifically our invention is a clamp and saw guide for holding a human patella and providing a guide so that a predetermined portion of the patella may be accurately removed by sawing.

The two largest and longest bones of the human body, the femur and tibia, meet at a person's knee. The tibia is situated at the front and inner side of the lower leg. It is prismoid in form, and expanded above where it enters into the knee joint. The head of the tibia is large and expanded on each side into two eminences, the condyles. These eminences form two smooth concave compartments or surfaces which articulate with the condyles of the femur. The medial condyle is more prominent anteriorly and broader both in the anterior-posterior and transverse diameters than the lateral condyle. Accordingly, the lateral articular surface of the tibia is shorter, more shallow and narrower than the medial surface of the tibia. The medial surface is broader, more circular, and concave from side to side. The anterior surfaces of the tuberosities are continuous with one another, forming a single large surface which is somewhat flattened. Posteriorly the tuberosities are separated from each other by a shallow depression for attachment of ligaments. The medial tuberosity presents posteriorly a deep transverse groove for the insertion of a tendon.

The patella is a sesamoid or lens shaped bone which slides in a groove between the condyles of the femur. Its function is to increase the efficiency of the quadriceps muscle by shifting the line of action of the muscle's pull forward. As the knee articulates, the muscles and tendons force the patella toward the condyles of the femur. Consequently, there is considerable relative motion between the patella and the other bones comprising the knee joint.

Because of aging or disease, the articulating surfaces of the knee may degrade. To treat certain pathologies, it has become common to surgically remove the condyles and replace these structures with prosthetic implants. By the same processes, the articulating surfaces of the patella may also degrade. In connection with the implantation of a prosthetic knee, therefore, the articulating surface of the patella may also be replaced. Because of the tendons connected to the patella, it is generally advisable to replace only the articulating surface. An ultra high molecular weight polyethylene articulating surface, with or without a metal baseplate, will be implanted on the posterior side of the patella, adjacent the femoral condyles. To implant such a prosthesis, the posterior surface of the patella is resected to produce a flat surface upon which the prosthesis can be mounted. In the past, the surgeon has often relied on skill of hand and eye in manipulating a sagittal saw to make an appropriate cut.

SUMMARY OF OUR INVENTION

We have invented a patella osteotomy guide for use by a surgeon in preparing a patella to receive a prosthetic articulating surface on the patella's posterior side. The osteotomy guide, according to our invention, captures a patella between jaws of a plier-like appliance. The jaws are curved for grasping a patient's patella, with a row of teeth facing inwardly from the jaws. The teeth are generally of pyramid shape, but a vertex of each tooth lies in a plane containing a bottom side of the respective jaw. This offset enables the teeth to grasp the patella in the middle. Each of the jaws has an integral saw capture slot extending along its length through which a sagittal saw may be inserted to precisely remove a selected portion of the patella. The tips of the jaws are extended so that the osteotomy guide may be used with larger patellas. A rotating, calibrated stylus accurately measures the position of the patella with respect to the integral saw capture slots. The stylus can be rotated so that a measurement can be made from the highest point of the patella, even if that point is asymmetrical with respect to the rest of the patella. In our preferred embodiment, the rotating stylus also functions as a pivot or fulcrum about which the jaws and handles of the osteotomy guide rotate. Handles for the osteotomy guide are offset from the plane of the jaws to allow hand access without interference with the patellar tendon of the patient. A threaded rod and thumb nut are provided on the handles so that the guide may be clamped to the patella.

The rotating stylus can be displaced up and down and then locked into a selected position using a draw bar and captured balls. We have also provided a bowed retaining ring which imparts a certain amount of preload to the stylus and draw bar assembly. Therefore, although the stylus can be easily rotated, it tends to remain in a selected position. This feature contributes to the ease with which the patella osteotomy guide can be adjusted for use.

In view of the foregoing, it is an object of our invention to provide a patella osteotomy guide with integral saw capture slots inclamping arms for improved blade control, so that level, predictable cuts may be made.

It is also an object of our invention to provide a patella osteotomy guide having a calibrated rotating stylus which can be locked into a desired position for precise bone resection.

Another important object of our invention is to provide a rotating stylus on a patella osteotomy guide which can be used to locate the thickest section of the patella.

Another object of our invention is to provide an adjustable stylus on an osteotomy guide which has a preloaded condition, so that the stylus can be rotated but tends to remain in a selected rotated position.

A further object of our invention is to provide a patella osteotomy guide having extended tips on the jaws to accommodate enlarged saw guides, whereby a greater range of patellae can be accommodated.

Yet another object of our invention is to provide a pliers-type patella osteotomy guide with offset handles allowing hand access to the apparatus without interfering with a patellar tendon.

These and other objects and features of our invention will be apparent from the following detailed description.

DETAILED DESCRIPTION OF OUR PREFERRED EMBODIMENT

We will now describe our preferred embodiment of our invention by reference to the accompanying drawings. Like numerals will refer to like parts in each drawing.

Figure 1:
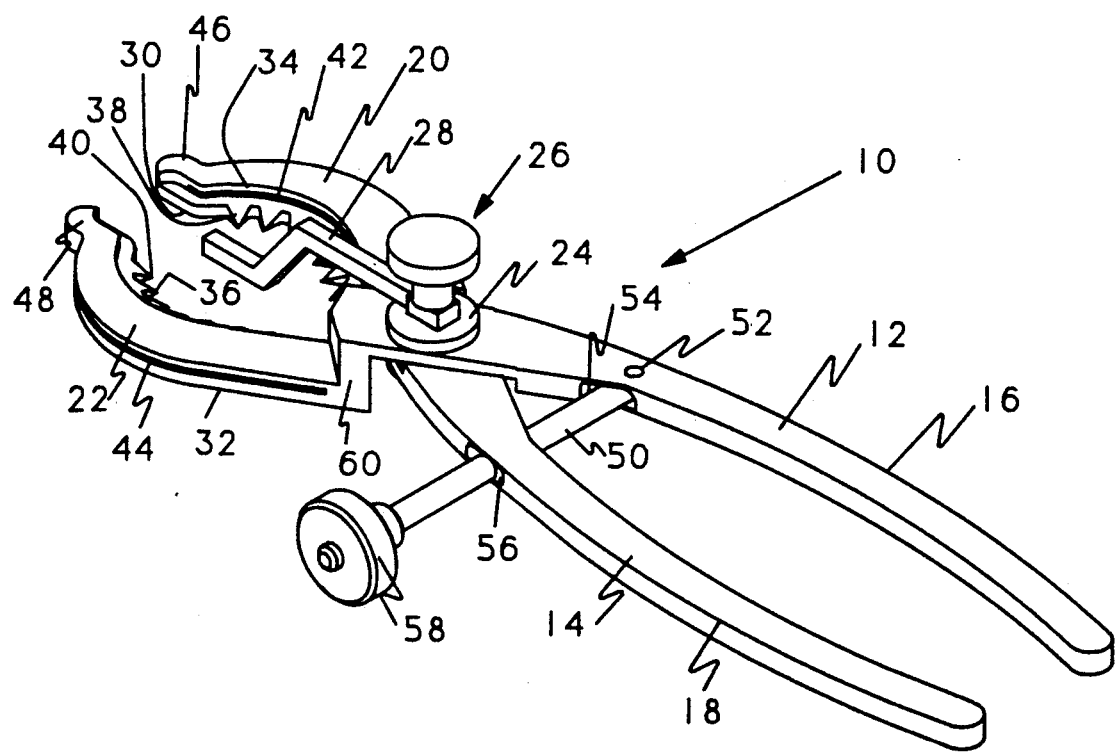
FIG. 1 is a perspective view of a patella osteotomy guide according to our present invention.

FIG. 1 is a perspective view of a patella osteotomy guide, generally labeled 10, according to our present invention. The osteotomy guide 10 comprises a pair of opposed clamping arms 12, 14. Each arm 12, 14 comprises a handle 16, 18 and opposed jaws 20, 22, respectively. The clamping arms are generally S-shaped, but of opposite hand and intersect a pivot or fulcrum 24 between the jaws and the handles. A stylus and draw bar assembly 26 serves as the pivot for the clamping arms and also supports a calibrated rotatable stylus 28. The stylus and draw bar assembly 26 will be more fully described hereafter. Each of the jaws 20, 22 has a generally planar under surface 30, 32 respectively. The under surfaces 30, 32 define a plane which will generally fall along the largest dimension of the patella when the osteotomy guide 10 is in use. The jaws 20, 22 are curved with concave inner sides 34, 36 which generally correspond to the expected anatomical shape of a patella. Along the concave sides 34, 36 there is a series of generally pyramid-shaped teeth 38 which are directed inwardly from the jaws. Each of the teeth forms a vertex 40 which will grip the patella when the jaws are closed about the patella. The vertices 40 preferably lie in the plane of the bottom surfaces 30, 32. This configuration tends to ensure that the teeth will grip the patella centrally, in the largest available dimension of bone. This minimizes the possibility that the patella may crumble or that pieces of the patella might be broken away by the forces generated during the osteotomy.

Each of the jaws 20, 22 has an integral saw capture slot 42, 44 extending along the length of the jaw. With the osteotomy guide secured to a patella, a surgeon can pass a sagittal saw through the saw capture slots to cut away a portion of the patella. Because human patellas are variable in size, each of the jaws has an extended tip 46, 48. These tips permit the slots 42, 44 to be extended beyond the curved portion of the jaws. This allows larger patellas to be gripped by more fully expanding the jaws away from one another while also accommodating smaller patellas. If fully rounded jaws of sufficient size to accommodate large patellas were used, the ends of the jaws might collide when the osteotomy guide was used with small patellas. The extended tips make it possible to accommodate a wider range of patella sizes, while still providing complete capture for a sagittal saw.

After the jaws 20, 22 have been manually placed on a patella, it is desirable to secure the guide in position. We have provided a threaded rod 50 and thumb nut 58 for this purpose. The threaded rod 50 is secured to one handle 12 with a pin 52. A slot 54 is provided in the handle so that the threaded rod may pivot slightly as the jaws of the osteotomy guide close. The threaded rod 50 passes through the other handle 14 through another slot 56. The thumb nut 58 can be tightened down along the rod to hold the handles together.

A patellar osteotomy is generally performed with the patella tendons in tact, or as in tact as possible, so that the function of the patella can be preserved. In order to reach the patella in its attached condition, and provide for manipulation of the osteotomy guide, we have offset the handles 12, 14 from the jaws 20, 22 with offset portions 60, 62. This provides room for a surgeon's hand or fingers to lie below the handles and yet to clear the patient's body as the jaws are placed around the patella.

Figure 2:
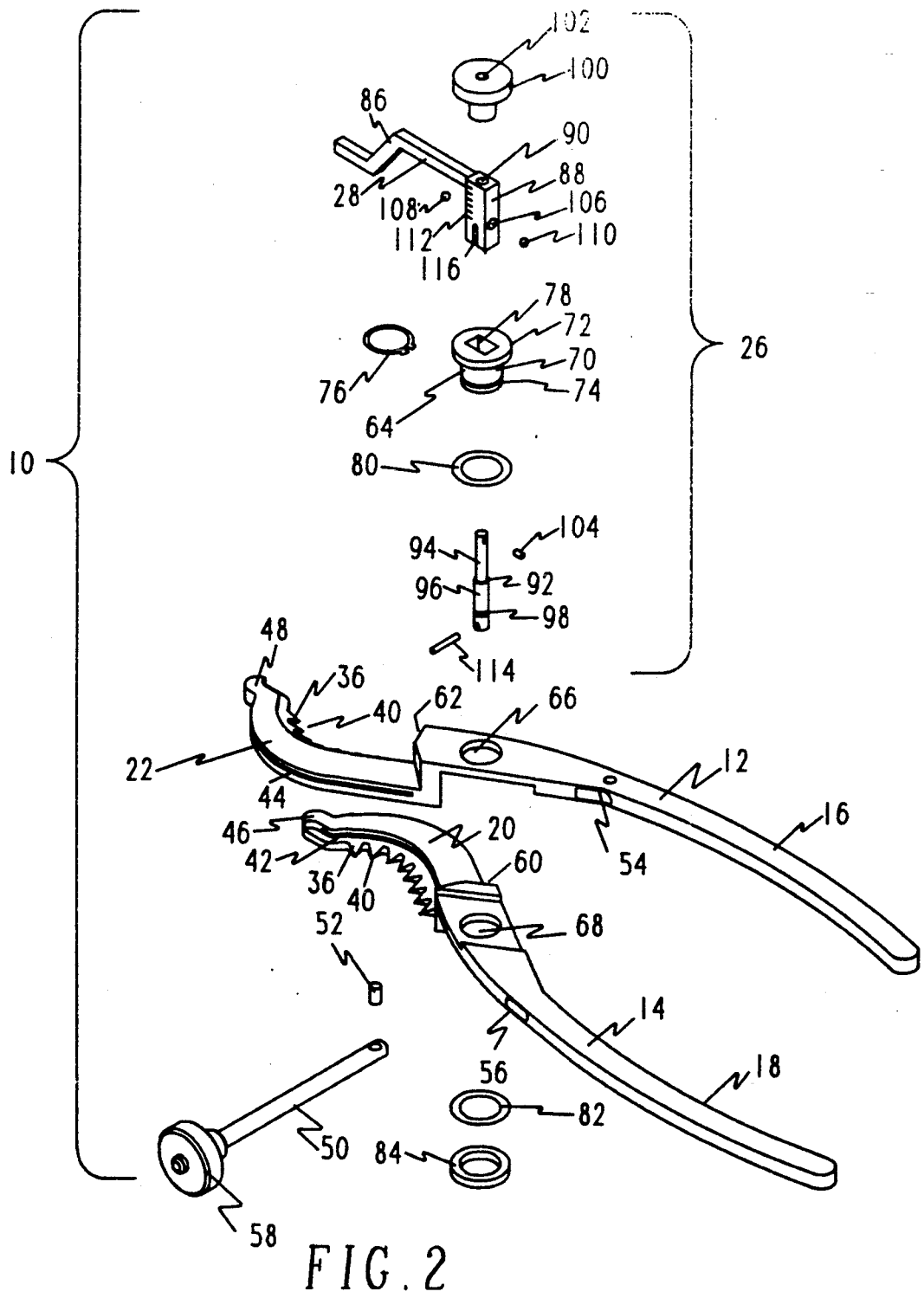
FIG. 2 is an exploded perspective view of the patella osteotomy guide of FIG. 1.

To achieve precise and predictable results with an osteotomy guide, it is important to remove only a predetermined amount of bone from the surface of a patella. To aid a surgeon in accomplishing this goal, we have provided the rotatable, calibrated stylus and draw bar assembly 26 mentioned above. We will now describe this assembly 26 with particular reference to FIG. 2. The stylus and draw bar assembly 26 comprises a scale bushing 64 which fits through bores 66, 68 at the fulcrum of the guide. The clamping arms 12, 14 of the guide pivot about this scale bushing. The bushing 64 comprises a cylindrical shaft 70 with an upper flange 72 and a lower annular slot 74 for receiving a bowed retaining ring 76. The function of the bowed retaining ring 76 will be more particularly described hereafter. A rectangular through bore 78 in the scale bushing 64 receives the stylus 28. There is a washer 80 which fits between the rim 72 and one of the arms 12. Another washer 82 is placed below the other arm 14 and above a spacer 84. When assembled, the spacer lies above the bowed retaining ring 76.

The stylus 28, which is supported by the scale bushing 64, comprises an arm 86 which is used to contact the highest part of the patella. The arm 86 is carried on a scale post 88, which has a rectangular cross-section and which fits slidingly, but snugly in the rectangular through bore 78 of the bushing 64. A vertical through bore 90 in the scale post 88 receives a scale draw bar 92. An upper portion 94 of the draw bar 92 is threaded. A lower portion 96 is preferably smoothly cylindrical except for an annular groove 98. The displacement of the scale draw bar 92 within the vertical through bore 90 is controlled by a scale adjustment knob 100 with a threaded bore 102 which mates with the upper portion 94 of the draw bar 92. A transverse pin 104 prevents the adjustment knob 100 from being completely removed. The scale post 88 also comprises a horizontal through bore 106. Two tungsten carbide precision balls 108, 110 are placed in the bore 106 on opposite sides of the scale draw bar 92. In this configuration, these balls 108, 110 rest in the annular groove 98. By displacing the scale draw bar, usually upwardly, the groove 98 will be displaced past the horizontal through bore 106, forcing the balls 108, 110 out against the rectangular through bore 78. This action will lock the scale post 88 in a selected position.

A calibrated scale 112 on the scale post 88 directly measure the amount of bone which would be removed. To keep the scale draw bar 92 from rotating when the scale adjustment knob 100 is turned, a lower transverse pin 114 passes through the scale draw bar and slides a vertical slot 116 in the scale post 88.

It will be apparent from the foregoing description that the stylus can be locked at a selected height or vertical displacement by manipulating the scale knob. Moreover, only a slight turn of the adjustment knob is necessary to secure the stylus in position. The scale post can be quickly slid to a desired position and then locked in the desired location without continual turning of the scale adjustment knob. With the vertical height or displacement set, the stylus can be rotated about an axis of the scale bushing so that the arm 86 of the stylus can be placed over the highest or most prominent part of the patient's patella. Because the split ring 76 is bowed, it provides a certain amount of tension in the scale bushing, restricting free rotation of the bushing. The stylus arm 86, therefore, will tend to stay in a selected angular orientation. At the same time, the vertical displacement of the stylus will be precisely locked. Using our invention, an orthopedic surgeon will be able to secure predictable and accurate resection of the patella.

Our invention may be embodied in other specific forms without departing from the spirit or essential characteristics thereof. The scope of our invention is to be defined by the appended claims, and not by the foregoing description and all changes which come within the meaning of equivalency of the claims are intended to be encompassed therein.

We claim as our invention:

1. An apparatus for guiding a sagittal saw during resection of a bone comprising
   means for gripping the bone;
   slot means integral with said gripping means for receiving a blade of the sagittal saw and defining a plane of resection for said sagittal saw; and
   means setting a depth of resection to be made in the bone by the sagittal saw, said depth setting means comprising
      a stylus for contacting an exposed surface of said bone;
      means for displacing said stylus in a linear direction substantially perpendicular to said plane of resection;
      means for locking said stylus at a selected linear displacement; and
      means for rotating said stylus about an axis parallel to said linear direction, said rotating means being operable independently of said displacing means and said locking means.

2. The apparatus according to claim 1 wherein the bone gripping means comprise opposed arms, each arm having a jaw and a handle, the opposed arms being pivotally joined at a fulcrum intermediate of said jaw and said handle.

3. The apparatus according to claim 2 wherein the jaws each comprise a generally planar bottom surface, said bottom surfaces being generally co-planar, and an opposed concave interior surface, said interior surface having a plurality of inwardly directed spikes, each spike defining at least one vertex for gripping the bone, said vertices lying substantially in the plane of said bottom surfaces.

4. The apparatus according to claim 3 wherein the jaws further comprise an extended tip at an end of the jaw remote from the fulcrum, said tip extending said slot means beyond said opposed concave interior surfaces.

5. The apparatus according to claim 1 wherein the rotating means comprise a pivoting cylinder having a bore parallel to an axis of said cylinder, said bore defining at least one interior wall and wherein the displacing means comprises a shaft slidably received within said bore.

6. The apparatus according to claim 5 wherein the shaft comprises an axial bore and wherein the locking means further comprise a draw bar slidably received within said axial bore, at least one means for engaging said interior wall, and means attached to said draw bar for urging said wall engaging means against said interior wall.

7. The apparatus according to claim 6 wherein the wall engaging means comprise a ball and wherein the urging means comprise a groove in said draw bar.

8. The apparatus according to claim 7 wherein the bone gripping means comprise opposed arms, each arm having a jaw and a handle, the opposed arms being pivotally joined at a fulcrum intermediate of said jaw and said handle.

9. The apparatus according to claim 8 wherein the jaws each comprise a generally planar bottom surface, said bottom surfaces being generally co-planar, and an opposed concave interior surface, said interior surface having a plurality of inwardly directed spikes, each spike defining at least one vertex for gripping the bone, said vertices lying substantially in the plane of said bottom surfaces.

10. The apparatus according to claim 9 wherein the jaws further comprise an extended tip at an end of the jaw remote from the fulcrum, said tip extending said slot means beyond said opposed concave interior surfaces.

11. The apparatus according to claim 8 wherein said pivoting cylinder is located at said fulcrum.

12. The apparatus according to claim 11 further comprising means for displacing said handles from a plane defined by said jaws.

13. The apparatus according to claim 12 wherein said pivoting cylinder further comprises means for providing a resistance to rotation of said cylinder.

14. The apparatus according to claim 13 wherein the resistance providing means comprise a spring-loaded, bowed split ring engaging an annular groove in said cylinder.

15. The apparatus according to claim 14 wherein the jaws each comprise a generally planar bottom surface, said bottom surfaces being generally co-planar, and an opposed concave interior surface, said interior surface having a plurality of inwardly directed spikes, each spike defining at least one vertex for gripping the bone, said vertices lying substantially in the plane of said bottom surfaces.

16. The apparatus according to claim 15 wherein the jaws further comprise an extended tip at an end of the jaw remote from the fulcrum, said tip extending said slot means beyond said opposed concave interior surfaces.

* * * * *